US009171129B2

(12) United States Patent
Cohen

(10) Patent No.: US 9,171,129 B2
(45) Date of Patent: Oct. 27, 2015

(54) SYSTEM AND METHOD FOR STORING, ACCESSING, AND DISPLAYING SPECIALIZED PATIENT INFORMATION AND OTHER MEDICAL INFORMATION

(76) Inventor: Todd J. Cohen, Port Washington, NY (US)

( * ) Notice: Subject to any disclaimer, the term of this patent is extended or adjusted under 35 U.S.C. 154(b) by 1903 days.

(21) Appl. No.: 11/054,870

(22) Filed: Feb. 10, 2005

(65) Prior Publication Data

US 2005/0177050 A1     Aug. 11, 2005

Related U.S. Application Data

(60) Provisional application No. 60/543,503, filed on Feb. 10, 2004.

(51) Int. Cl.
*G06F 3/02* (2006.01)
*G06F 19/00* (2011.01)

(52) U.S. Cl.
CPC ................................. *G06F 19/322* (2013.01)

(58) Field of Classification Search
CPC . A61B 5/0022; A61B 5/0205; G06F 19/3418
USPC .................................. 600/301, 509, 515, 519
See application file for complete search history.

(56) References Cited

U.S. PATENT DOCUMENTS

| 4,838,275 | A | * | 6/1989 | Lee ................................. 600/483 |
| 5,822,544 | A | * | 10/1998 | Chaco et al. ....................... 705/2 |
| 6,364,834 | B1 | * | 4/2002 | Reuss et al. .................... 600/300 |
| 6,385,589 | B1 | * | 5/2002 | Trusheim et al. .................. 705/2 |
| 6,665,559 | B2 | | 12/2003 | Rowlandson |
| 6,793,625 | B2 | | 9/2004 | Cavallaro et al. |
| 6,804,656 | B1 | * | 10/2004 | Rosenfeld et al. ................ 705/3 |
| 2002/0188213 | A1 | | 12/2002 | Bardy |
| 2002/0198473 | A1 | * | 12/2002 | Kumar et al. .................. 600/595 |

OTHER PUBLICATIONS

Notification of Transmittal of the International Search Report and the Written Opinion of the International Searching Authority, or the Declaration.

* cited by examiner

*Primary Examiner* — Christopher D Koharski
*Assistant Examiner* — Michael D Abreu
(74) *Attorney, Agent, or Firm* — Greenberg Traurig, LLP

(57) ABSTRACT

The invention provides a system and method of providing a user with specialized patient information comprising: uploading, storing, requesting, receiving, and displaying cardiological patient information for a patient. The display of the cardiological information is configured to optimal care to be provided to a patient.

13 Claims, 20 Drawing Sheets

Entering Patient Information - Confirm Patient Information - Upload ECG - Upload HeartPass Agreement - Finished Patient Information: This information is not displayed on HeartPass reports or queries:

- HeartPass Password — 410
- Last Name — 412
- First Name — 414
- Address Line 1
- Address Line 2
- City — 416
- State
- Zip Code
- Date of Birth (MM/DD/YY) — 418
- Email Address — 420

Past Medical History — 422
- ☐ Hypertension
- ☐ Diabetes
- ☐ Asthma
- ☐ Chronic Obstructive Pulmonary Disease
- ☐ Chronic Renal Insufficiency
- ☐ Hemodialysis
- ☐ Cerebral Vascular Accident
- ☐ Transient Ischemia Attack
- ☐ CNS Bleed
- ☐ GI Bleed
- ☐ Anemia
- ☐ Deep Vein Thrombosis
- ☐ Pulmonary Embolus
- ☐ Inferior Vena Cava Filter
- ☐ Carotid Endarterectomy Malignancies: — 424
Miscellaneous: — 426
Allergies: — 428
Medications: — 430

Cardiac History — 432
- ☐ Neurocardiogenic Syncope
- ☐ Orthostatic Syncope
- ☐ Syncope due to Autonomic Dysfunction
- ☐ Coronary Artery Disease
- ☐ Myocardial Infarction
- ☐ Coronary Artery Bypass Grafting
- ☐ Aortic Valve Replacement
- ☐ Mitral Valve Replacement
- ☐ Cardiomyopathy
- ☐ HOCM/IHSS
- ☐ Cardiac Transplant
- ☐ Abdominal Aortic Aneurysm
- ☐ AAA Repair
- ☐ Congestive Heart Failure
- Ejection Fraction
- ☐ Percutaneous Coronary Intervention, enter details below

- 436 ☐ Permanent Pacemarker (PPM)
- ☐ ICD
- 438 ☐ BiVentricular Device — 434
- 440 ☐ Implantable Loop Recorder
- Manufacturer: None
- 442

Please check accuracy of above information. If it is correct please press the button below.
■ — 444

FIG. 5

Entering Patient Information - Confirm Patient Information - Upload ECG - Upload HeartPass Agreement - Finished Patient Information: This information is not displayed on HeartPass reports or queries:

HeartPass Password [          ]
Last Name [          ]
First Name [          ]
Address Line 1 [          ]
Address Line 2 [          ]
City [          ]
State [          ]
Zip Code [          ]
Date of Birth (MM/DD/YY) [          ]
Email Address [          ]

Past Medical History
- ☐ Hypertension
- ☐ Diabetes
- ☐ Asthma
- ☐ Chronic Obstructive Pulmonary Disease
- ☐ Chronic Renal Insufficiency
- ☐ Hemodialysis
- ☐ Cerebral Vascular Accident
- ☐ Transient Ischemia Attack

- ☐ CNS Bleed
- ☐ GI Bleed
- ☐ Anemia
- ☐ Deep Vein Thrombosis
- ☐ Pulmonary Embolus
- ☐ Inferior Vena Cava Filter
- ☐ Carotid Endarterectomy Malignancies: [          ]
Miscellaneous: [          ]
Allergies: [          ]
Medications: [          ]

Cardiac History
- ☐ Neurocardiogenic Syncope
- ☐ Orthostatic Syncope
- ☐ Syncope due to Autonomic Dysfunction
- ☐ Coronary Artery Disease
- ☐ Myocardial Infarction
- ☐ Coronary Artery Bypass Grafting
- ☐ Aortic Valve Replacement
- ☐ Mitral Valve Replacement

- ☐ Cardiomyopathy
- ☐ HOCM/IHSS
- ☐ Cardiac Transplant
- ☐ Abdominal Aortic Aneurysm
- ☐ AAA Repair
- ☐ Congestive Heart Failure
  Ejection Fraction [          ]

- ☐ Percutaneous Coronary Intervention, enter details below
  [          ]

- ☐ Permanent Pacemarker (PPM)
- ☐ ICD
- ☐ BiVentricular Device
- ☐ Implantable Loop Recorder
  Manufacturer [ None ▪ ]

*FIG. 5A*

Please check accuracy of above information. If it is correct please press the button below.

HeartPass Number 132 ◄────── 510

Entering Patient Information - <u>Confirm Patient Information</u> - Upload ECG - Upload HeartPass Agreement - Finished

| Past Medical History | Cardiac History |
|---|---|
| Allergies -<br>Medications - | |

Please note the patient's Heartpass Number above. Click below to begin the upload ECG process.

[ Continue to Next Step ] ◄────── 520

If the information is INCORRECT, please hit the button below to edit the information entered.

[ Edit Information ] ◄────── 522

Enter Payment Information:
Please Note, information will not be active unless this transaction is approved.

HeartPass User ID - _____ —— 710

| | | |
|---|---|---|
| HeartPass 1 Year Charge | 99.95 | |
| HeartPass User ID | 132 | — 712 |

| | | |
|---|---|---|
| Credit Card Number | | |
| Expiration Date | 01 January ▼ | |
| Expiration Date | 2004 ▼ | — 714 |
| CW Number | | |

Submit

Heartpass Provider _____ 50
Provider ID _____
[A|B|C|D|E|F|G|H|I|J|K|L|M|N|O|P|Q|R|S|T|U|V|W|X|Y|Z]

| userid | h_userid | h_lastname | h_firstname | h_dob | Show Heartpass | Edit Heartpass |
|---|---|---|---|---|---|---|
|  | AAA | Anzalone |  | 11/03/30 | Display | Edit ECG |
|  | AAA | Alt |  | 07/13/26 | Display | Edit ECG |
|  | AAA | Anzalone |  | 01/27/35 | Display | Edit ECG |

Heartpass Provider _____
Provider ID 6
Next Page

| userid | h_userid | h_lastname | h_firstname | h_dob | Terminate | Renew | Enroll Date | Expiry Date | Active |
|---|---|---|---|---|---|---|---|---|---|
| 32 | AAAA0001 | Pandola | Anthony | 04/18/38 | Terminate | Renew | 20050101 | | Active |
| 33 | AAAA0002 | Fulfarr | Anna | 02/18/24 | Terminate | Renew | 20050101 | | Active |
| 34 | AAAA0003 | Jantz | Valerie | 11/07/51 | Terminate | Renew | 20050101 | | Active |
| 35 | AAAA0004 | Anzalone | Vincent | 11/03/30 | Terminate | Renew | 20050101 | | Active |
| 36 | AAAA0005 | Salvador | Rita | 08/20/27 | Terminate | Renew | 20050101 | | Active |
| 37 | AAAA0006 | Campbell | Patricia | | Terminate | Renew | 20050101 | | Active |
| 38 | AAAA0007 | Grado | Mary | 11/21/21 | Terminate | Renew | 20050101 | | Active |
| 39 | AAAA0008 | Jantz | Harold P | 04/15/49 | Terminate | Renew | 20050101 | | Active |
| 40 | AAAA0009 | McNulty | Joseph | | Terminate | Renew | 20050101 | | Active |
| 41 | AAAA0010 | Shorton | Barry | 04/14/38 | Terminate | Renew | 20050101 | | Active |
| 42 | AAAA0011 | Alt | Willian | 07/13/26 | Terminate | Renew | 20050101 | | Active |
| 43 | AAAA0012 | Anzalone | Patsy | 01/27/35 | Terminate | Renew | 20050101 | | Active |
| 44 | AAAA0013 | Bailey | Willian | 05/20/60 | Terminate | Renew | 20050101 | | Active |
| 45 | AAAA0014 | Banks | McKinley | 04/04/29 | Terminate | Renew | 20050101 | | Active |
| 46 | AAAA0015 | Baur | James | 10-25-56 | Terminate | Renew | 20050101 | | Active |
| 47 | AAAA0016 | Brown | James | 05/14/39 | Terminate | Renew | 20050101 | | Active |

*FIG. 11A*

HOME | LOGIN | DEMO | EDUCATION | CONTACT US

HOME
   Home
   News

REGISTER
   Register

LOGIN
   PATIENTaccess
   DOCTORaccess
   Logout

DEMO
   View Demo

EDUCATION
   Arrhythmia
   Common Diseases
   Procedures
   CPR Info
   Links
   Lifestyle
   Risk Factors
   Stroke
   Your Heart CONTACT US
   Background
   Investor Relations
   Contact Info.

Username: [ ]
Password: [ ]
[Login]

*FIG. 14*

HOME | LOGIN | DEMO | EDUCATION | CONTACT US

HOME
  Home
  News

REGISTER
  Register

LOGIN
  PATIENTaccess
  DOCTORaccess
  Logout

DEMO
  View Demo

EDUCATION
  Arrhythmia
  Common Diseases
  Procedures
  CPR Info
  Links
  Lifestyle
  Risk Factors
  Stroke
  Your Heart CONTACT US
  Background
  Investor Relations
  Contact Info.

You are logged in,

Search ECGAccess Database by LAST Name - Only Exact Matches are returned.

Search Name: [               ] [ Search ]

List All your patients. If you have many patients, this list might take a long time to download depending on your internet connection.

List All My Patients

*FIG. 15*

HOME | LOGIN | DEMO | EDUCATION | CONTACT US

HOME
  Home
  News

REGISTER
  Register

LOGIN
  PATIENTaccess
  DOCTORaccess
  Logout

DEMO
  View Demo

EDUCATION
  Arrhythmia
  Common Diseases
  Procedures
  CPR Info
  Links
  Lifestyle
  Risk Factors
  Stroke
  Your Heart CONTACT US
  Background
  Investor Relations
  Contact Info.

You are logged in,

Connected to database successfully, Displaying Search Results

| id | dob | lastname | firstname | filename1 | filename4 |
|---|---|---|---|---|---|
|  | 11/26/75 |  | Ronald | Show ECG | ron |
|  | 11/25/75 |  | Ronald | None | rlo |

If no results are shown, please return to the search menu and search again.

Return to search menu

FIG. 16

SYSTEM AND METHOD FOR STORING, ACCESSING, AND DISPLAYING SPECIALIZED PATIENT INFORMATION AND OTHER MEDICAL INFORMATION

CROSS-REFERENCE TO RELATED APPLICATIONS

This application claims the benefit of the filing date of U.S. provisional application Ser. No. 60/543,503 entitled SYSTEM AND METHOD FOR STORING AND ACCESSING ELECTROCARDIOGRAMS AND OTHER MEDICAL INFORMATION, to Todd J. Cohen, M. D. filed Feb. 10, 2004, and the complete contents of that application are incorporated herein by reference.

BACKGROUND OF THE INVENTION

A physician or other health care professional requires accurate and relevant information about a patient in order to provide optimal care. This information is helpful when a person needs emergency treatment. For example, if a person is experiencing a cardiac event such as a heart attack, palpitations, lightheadedness or dizziness, or loss of consciousness, their cardiac information may not be available. The emergency medical treatment given to this person would be greatly enhanced if it were possible for the treating professional to obtain valuable diagnostic information about the person's cardiologically relevant medical history even in the event that it is not available from the afflicted person or someone speaking on his or her behalf.

The present invention relates generally to medical data and more particularly to methods and systems for storing and accessing medical data, such as electrocardiograms. The electrocardiogram (ECG) is a routine test and tool performed and used by almost every physician, hospital, medical clinic, and health provider. An ECG records changes in the electrical field evolving from the heart and contains basic information regarding the status of one's heart. Heart disease is the number one cause of medical illness, morbidity, and mortality worldwide. An ECG is pivotal in the diagnosis and treatment of every type of illness that might afflict the heart, such as myocardial ischemia (the lack of blood flow and oxygen to the heart) and myocardial infarction (heart attack), as well as illnesses that might afflict other organs, such as the lungs and the brain.

The electrocardiogram information is a critical part of one's medical record, which would only be interpreted by a trained medical professional. Electrocardiogram information can help identify critical events and provide information for diagnosing heart rhythm disturbances. In the setting of chest pain or discomfort, shortness of breath, lightheadedness or dizziness, palpitations, and/or loss of consciousness your ECG may show an abnormality in heart muscles, its wiring or its rhythm.

The ability to compare a patient's previous ECG with the patient's most recent ECG is of great value, as it enables a practitioner to assess any change in the cardiac profile of a patient. Often it is only after comparing a recent ECG with a prior ECG (which may not be available) that a definitive diagnosis can be made. A prior ECG can make the difference in a patient receiving unnecessary drugs, tests, and procedures and help focus the doctor to the appropriate treatment. In the extreme situation, such as an emergency, getting a new ECG from a patient takes time and the immediate availability of a previous ECG is extremely helpful. Moreover, a diagnosis based on a patient's newer ECG is uncertain without the comparison to a previous ECG (a baseline ECG). Unfortunately, it is often difficult to obtain a patient's previous ECG, and unless the patient is visiting his or her regular cardiologist, a new ECG is required in all cases and is the only data point for the diagnostician.

Therefore, a need exists for an improved system or method of providing patients and physicians with access to medical histories, such as the previous electrocardiograms of patients, which overcomes drawbacks of the prior art.

SUMMARY OF THE INVENTION

The invention provides a method of providing a user with specialized patient information comprising: uploading specialized patient information for a patient into a secure database, storing said specialized patient information in said database, receiving a request for said specialized patient information from a user, transmitting said requested specialized patient information to said user to allow said user to display the specialized patient information; wherein said specialized patient information is configured to display the specialized information such that optimal health care can be provided to the patient. The transmitted specialized patient information may be stored on a storage device. The method may include confirming the specialized patient information uploaded into said database. Access to the database may be prevented until a user identifier is provided. The provision of a password may be required combination with the user identifier. The specialized patient information may comprise cardiological patient information. The specialized patient information may comprise neurological patient information, psycho-centric patient information, nephrological patient information, radiological patient information, musculo-skeletal patient information, oncological patient information, patient information related to internal medicine, endocrinological patient information, or gastroenterological patient information.

The specialized patient information may further include an image. The cardiological patient information can further include an electrocardiogram. The specialized patient information may also include patient identification information. The specialized patient information may include a patient history. Included in the cardiological patient information can be a patient history comprising a medical history of the patient, the medical history comprising a cardiologically relevant factor. Also included in the cardiological patient information can be a patient history comprising cardiac history of the patient, and this cardiac history includes a cardiologically relevant factor. The cardiologically relevant factor may further comprise the history of an implant.

According to the method, the display of cardiological patient information may comprise an electrocardiogram, a patient history comprising a medical history of the user including a cardiologically relevant medical history factor and a cardiac history including a cardiologically relevant cardiac history factor.

The method can include enrolling a patient into said database. Where a user includes the patient, the patient may be prevented from altering the displayed information. According to the method, a user who is a health care professional may be permitted to alter the stored specialized patient information. A user may also be a provider of the method. The provider can be a heath care professional. The health care professional may be offered the option to enroll a patient into said database, and the health care professional may be offered the option to access the stored specialized patient information of a patient associated with the health care professional. The stored specialized patient information of a patient associated with the health care professional is searchable by a user identifier. Access may be provided to an entity giving emergency treatment to the enrolled patient.

In another embodiment, the invention provides a system for visually presenting cardiological patient information comprising a computer executable program and a program memory for storing cardiological patient information. The program, when executed by a processor is structured to accept, via an input, specialized patient information about a patient, store said specialized patient information in said database, receive via the input a request for said specialized patient information from a user, transmit via an output said requested specialized patient information to said user to allow said user to display the specialized patient information, wherein said specialized patient information is configured to display the specialized information such optimal health care can be provided to a patient. The memory may be in a secure environment, and the memory can be remotely located. The requested specialized patient information can be transmitted via the internet.

Figure 3:
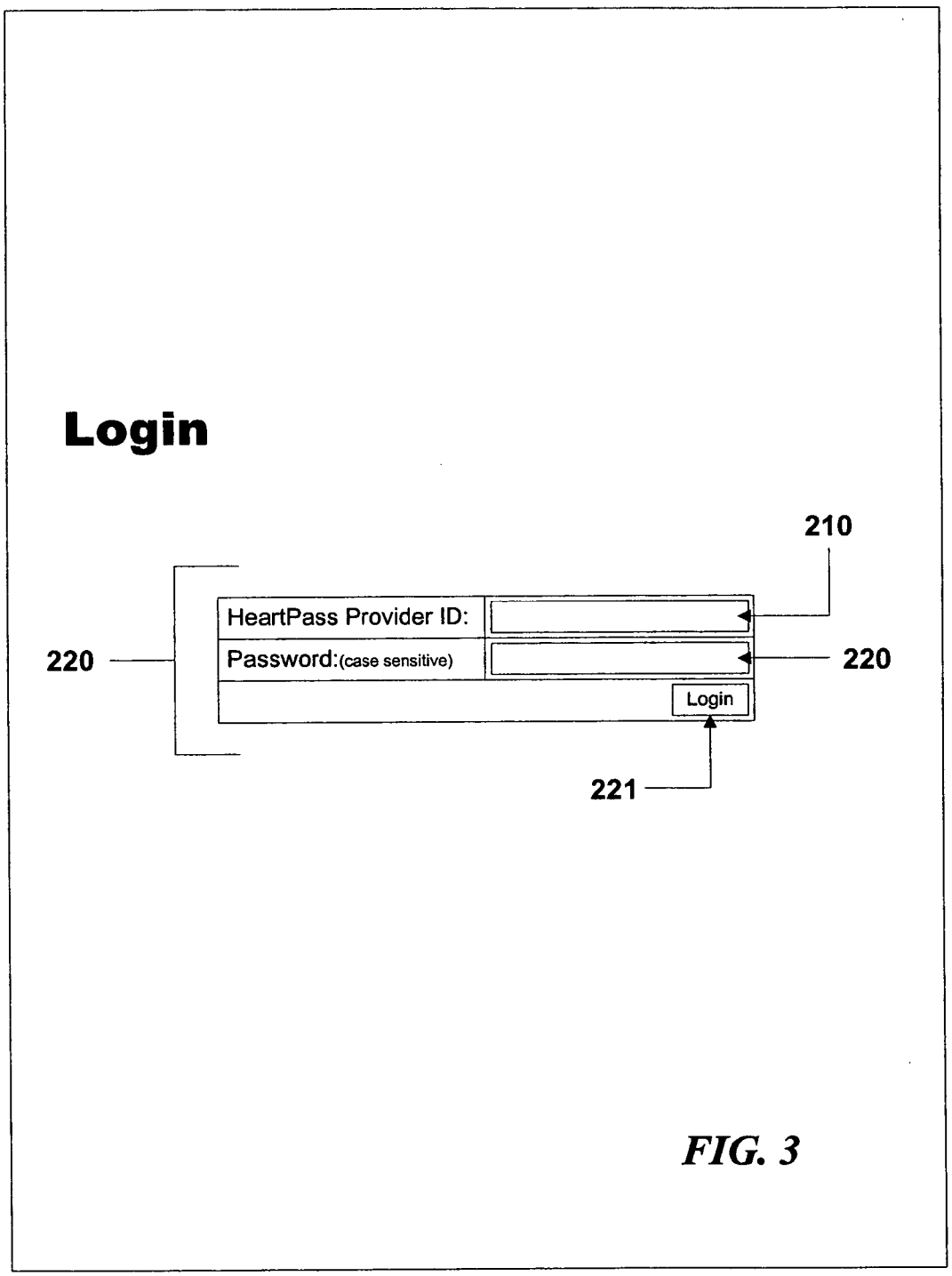

At FIG. 3 is shown the displayed webpage when a user selects the "Provider Login".

Figure 4:
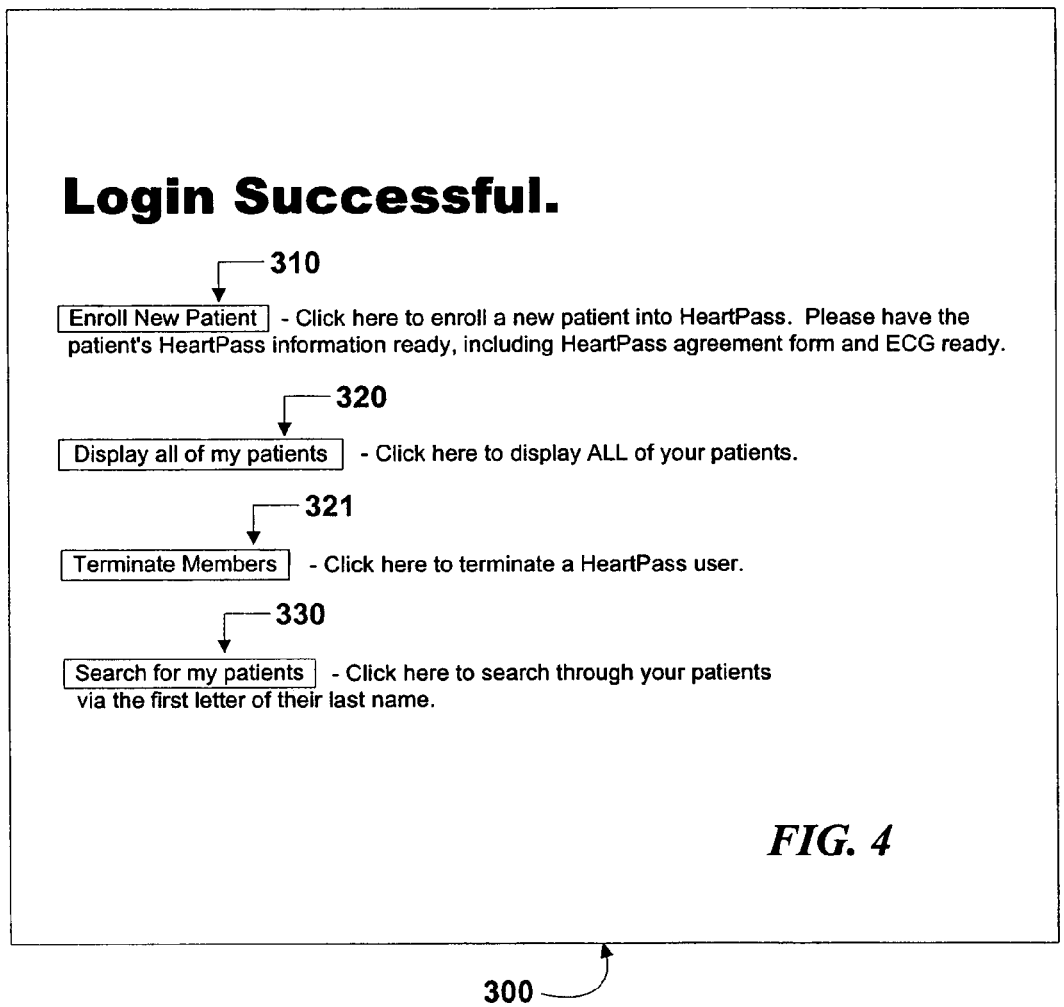

FIG. 4 shows a web page that gives a number of options that are a function of the degree of a provider's access.

FIG. 5 is shown the page displayed when the provider is given the option to enroll a new user into the database.

FIG. 6 shows a web page that allows a provider to confirm information entered about the enrolling user that is displayed there.

Figure 7:
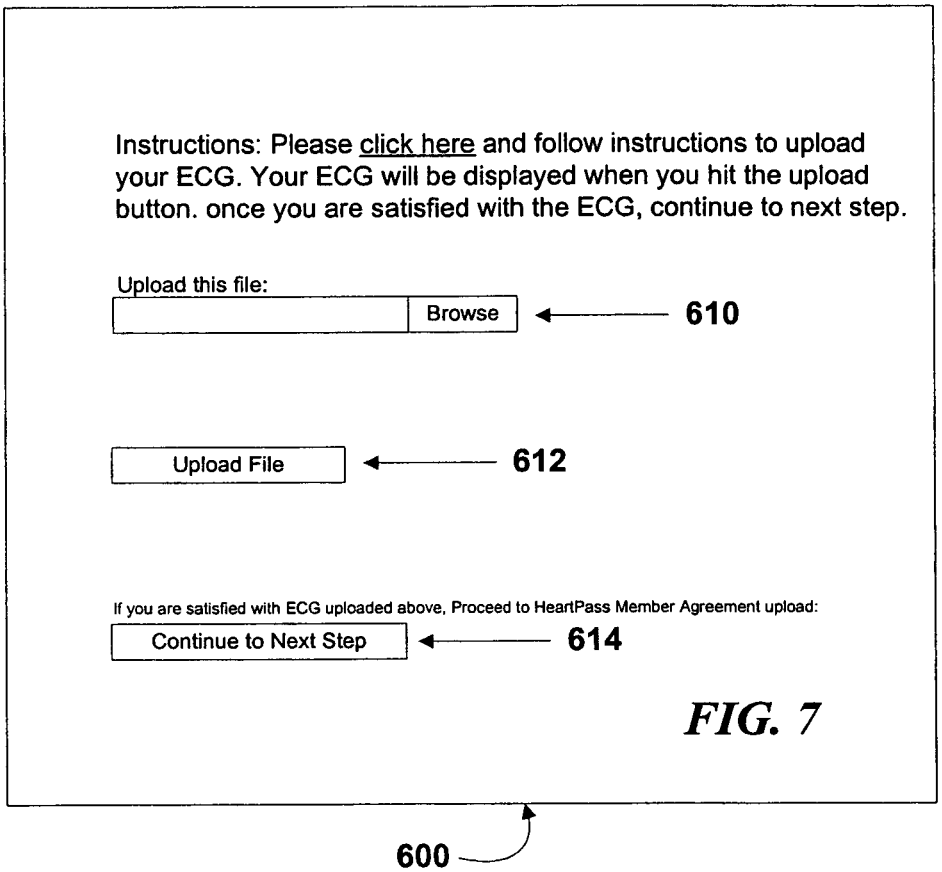

FIG. 7 shows a web page where the provider can upload an ECG into the database.

Figure 9:
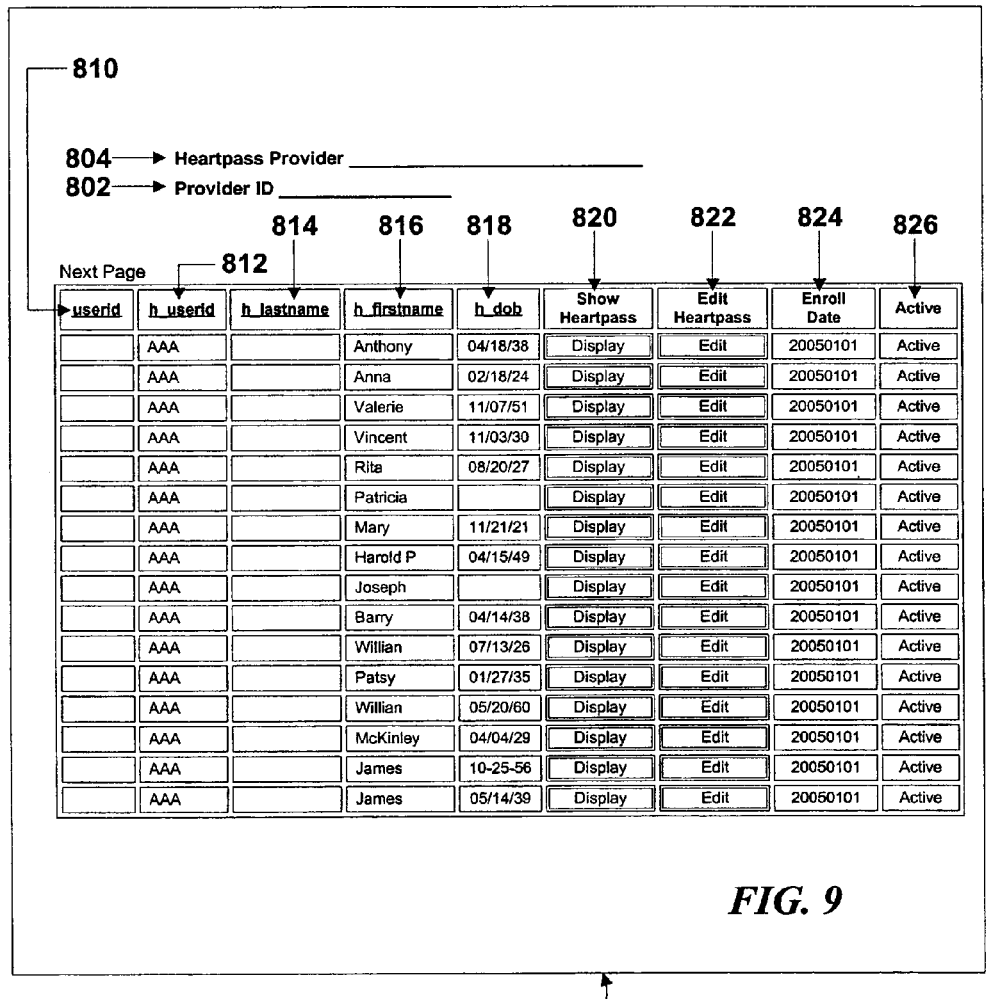

At FIG. 8 is shown a page for entering payment information in order to process a payment FIG. 9 shows a web page where the users associated with the provider may all be presented as indexed by any number of useful categories that identify or classify the patient.

Figure 10:
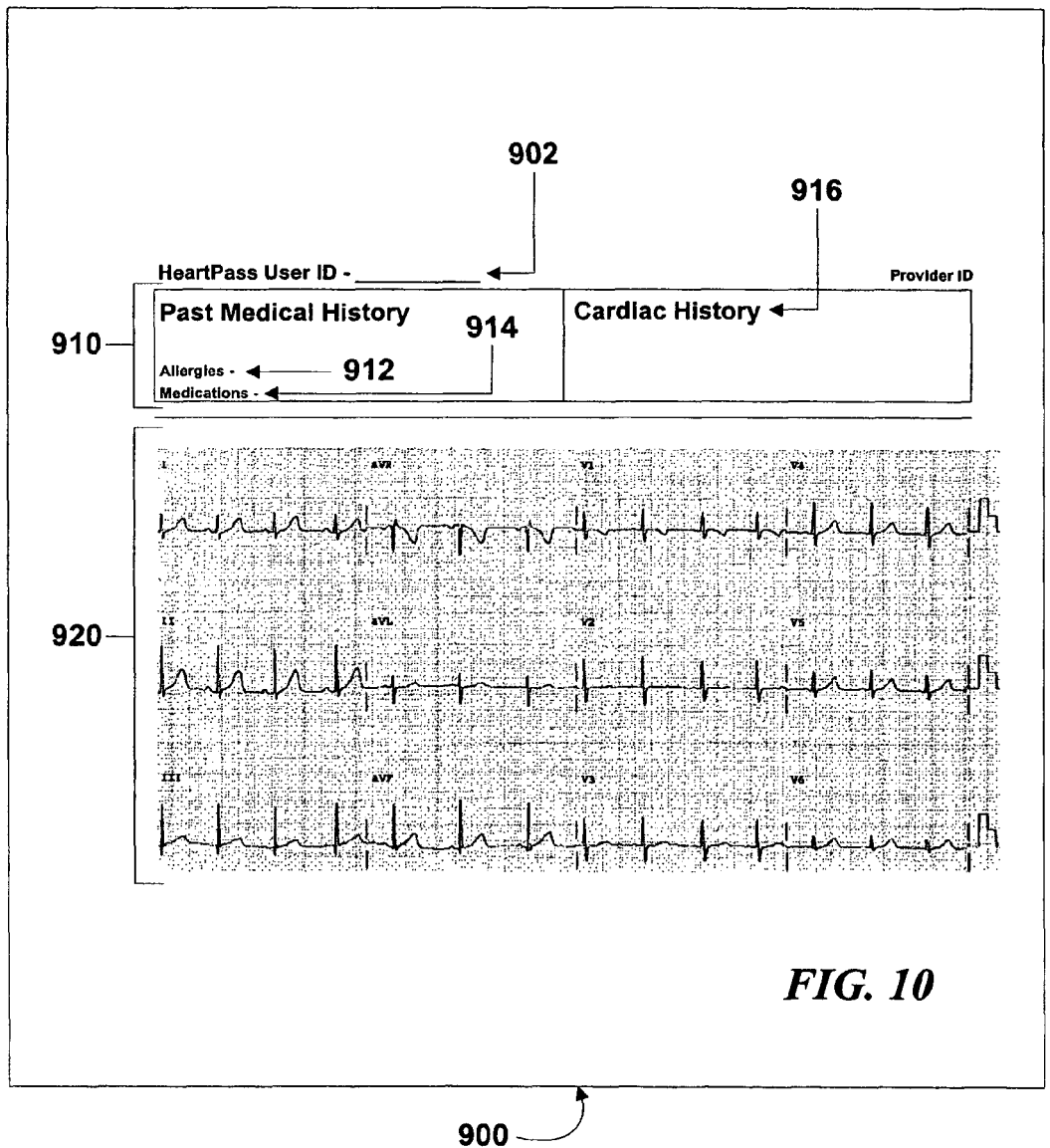
Figure 10A:
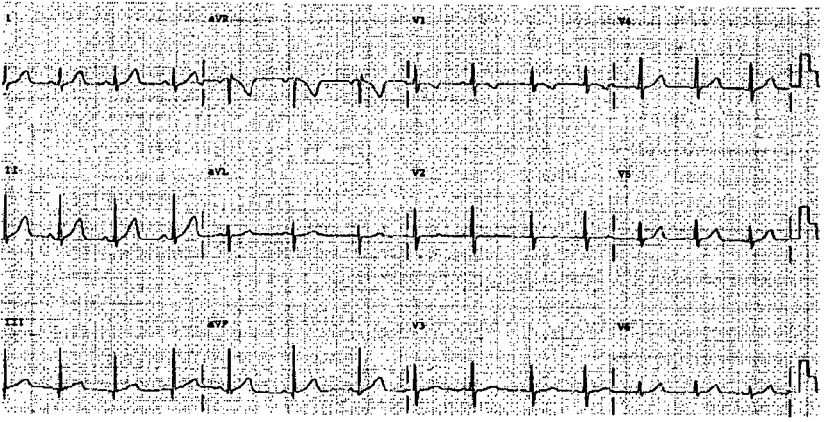

FIG. 10 shows a display of the cardiological patient information that is configured to enable optimal care to be provided to a patient.

FIG. 11 shows a web page where users are presented by last name in alphabetical order, with a linked alphabetized index.

Figure 12:
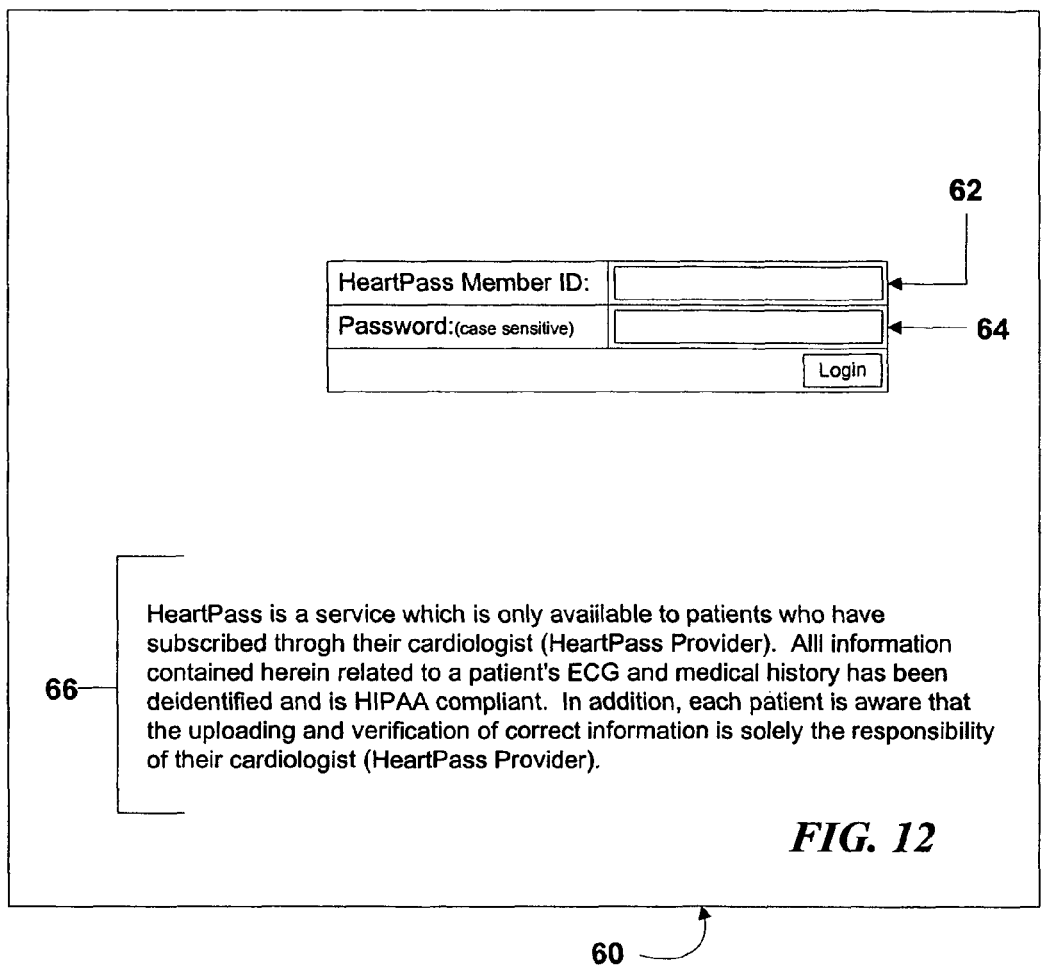

FIG. 12 shows a web page where an enrolled user who is not a health care professional or provider can access their stored information, via a login page.

Figure 13:
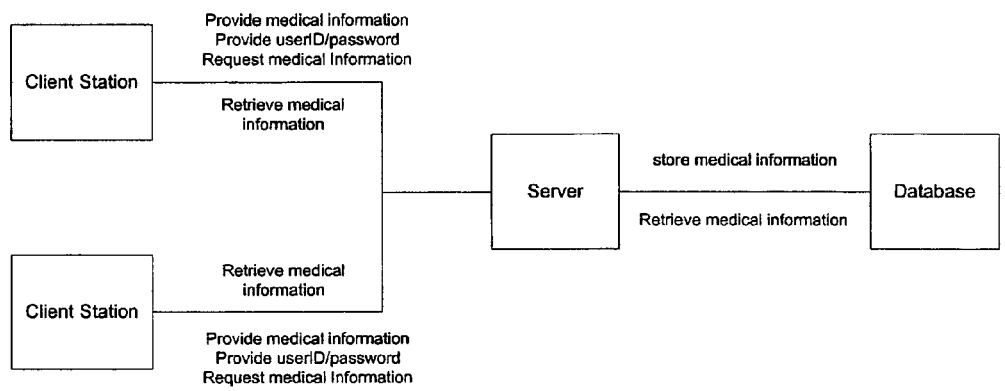

FIG. 13 is an illustration of the components of the system according to one embodiment of the present invention.

FIG. 14 illustrates the log in query box on a web site according to one embodiment of the present invention.

FIG. 15 illustrates the search query box to request the medical information of a patient on a web site according to one embodiment of the present invention.

FIG. 16 illustrates the information resulting from the search query entered by a user on a web site according to one embodiment of the present invention.

Figure 17:
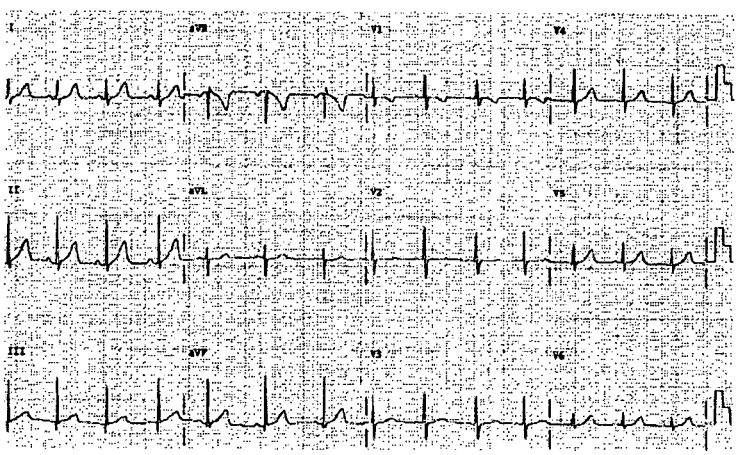

FIG. 17 illustrates an electrocardiogram of a patient as requested by the user on a web site according to one embodiment of the present invention.

DETAILED DESCRIPTION OF THE INVENTION

In accordance with the invention, a system and method is provided for providing access to previously stored medical data, such as the electrocardiograms of patients, and displaying that information in a manner that allows a heath care professional to provide optimal treatment. Certain embodiments of the invention provide patients and physicians with secure electronic access over a network, such as the internet, to the previously stored electrocardiograms of patients. In this manner, the present invention can allow a doctor to access quickly an electronic copy of a patient's prior ECG or other medical records to compare with a patient's current ECG to more effectively diagnose a patient's condition and focus the doctor on the proper treatment. The manner in which the electronic records are presented to a health care professional allows him or her to swiftly analyze a patient's condition and quickly apply the correct course of treatment. Unnecessary testing and/or diagnostic measures can be avoided, as well as treatments that can prove harmful to a patient in the absence of the ready, relevant information in one place or presentation.

Figure 1:
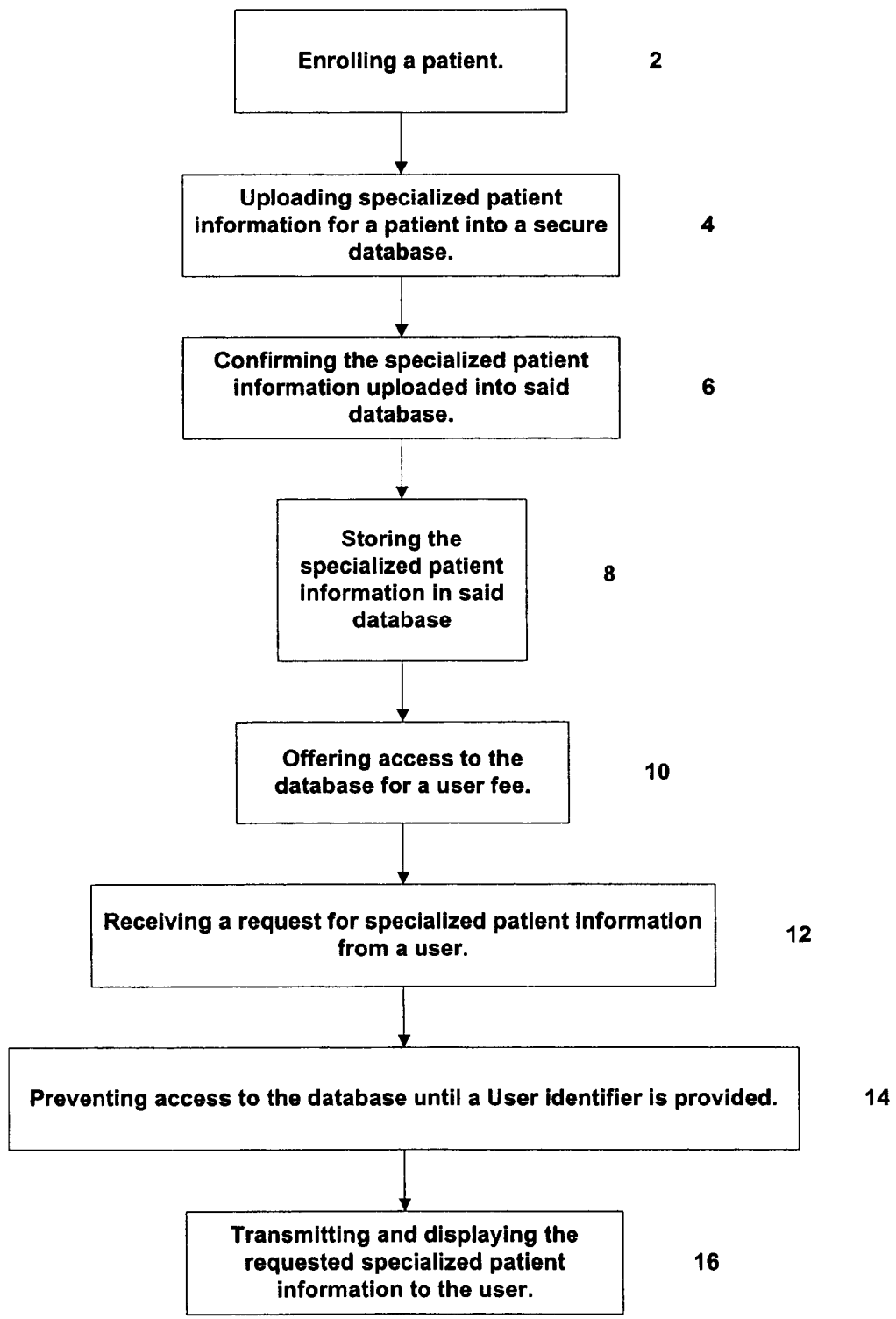
FIG. 1 is a high-level flow chart of one embodiment of the method.

One embodiment of the present invention is directed to a client-server system and/or method for providing a user with electronic access over a network to medical history information. As shown in FIGS. 1 and 13 this embodiment of the present invention can include a storage medium having electrocardiogram or other medical information stored thereon, such as a database or file. It should be understood that the storage medium can utilize any logical arrangement of medical or related data and such data may be arranged in fewer or more tables, databases, or files. Further, such data could be stored, as part of any one or more of the components of the present invention, and any of the one or more databases could be accessible, via a communicative coupling, to any of the aforementioned components of the present invention.

FIG. 1 is a flow chart showing one exemplary embodiment of the method for providing a user with specialized patient information. Specialized information about a patient refers to information that is related to a given subject, specialty, or aspect of a patient's health. A patient, as used herein, refers to any subject whose information is used in the invention, since the subject's information is related to optimizing the treatment and health of the subject. It is not necessary that a subject be under the care of a given health care professional or that the patient is awaiting medical treatment for the subject to be a patient as that term is used in the present invention. It is enough that the information itself is related to the health of the subject and may be used to optimize the treatment and health of the subject should the need or desire arise. Thus if an insurance company were to make use of a subject's specialized information in the database, it would still be specialized patient information. The specialized patient information described in exemplary embodiments of the present invention includes cardiological patient information. Cardiological, as used herein, means of or pertaining to cardiology. Cardiology is the study of the heart and its action and diseases. As used herein, cardiological information refers broadly to any information relating to heart health, and cardiological information about a patient means information that related to or useful in analyzing the heart health about a given patient. Finally, use of the article "a" as used herein includes both the singular and the plural unless otherwise indicated. For example such, "a patient" can comprise one patient or more than one patient. Similarly, as used herein, the singular form of a noun or pronoun shall be considered to include within its meaning the plural form of a noun or pronoun so used.

The method begins by enrolling a patient 2 so that specialized information about that patient can be stored in and accessed from a database. When enrolling the patient, cardiological information about the patient can be uploaded 4 into the secure database. Once the patient is enrolled and the cardiological information is uploaded into the database, the information may then be reviewed and confirmed 6. The method then moves to storing the cardiological patient information in the database. 8. Access to the stored information may then be offered to a user for a fee 10.

According to the method, a user can access the stored cardiological patient information, as for example via a user interface configured to allow a user to request 12 the stored information. Access to the database may be denied unless an identifier of some sort is provided 14, including a user identifier such as a provider identifier, a patient identifier or a member identifier, or an administrator code. This can enhance the security of the database as well as allows for better control of the content and manner in which the patient information that is accessed. Once the request for patient information is received 12, the requested information can be transmitted and displayed to the user 16. This embodiment of the present invention can include a client station, including, but not limited to a computer, telephone, scanner, cell phone, facsimile machine, PDA or other internet equipped processing device, having a user interface configured to allow a user to request stored specialized patient information. Once requested, the display of the cardiological information, no matter the media on which it is presented, is configured to enable a heath care professional to provide optimal care. A health care professional, as used herein, refers broadly to any person having training in providing health care service. While physicians, nurses, and emergency medical technicians are well known examples of health care professionals, anyone trained to provide treatment whose aid would be enhanced by virtue of the displayed information is encompassed by the term.

One embodiment of the invention is shown in the context of a number of web pages, as shown in FIGS. 2 to 12.

Figure 2:
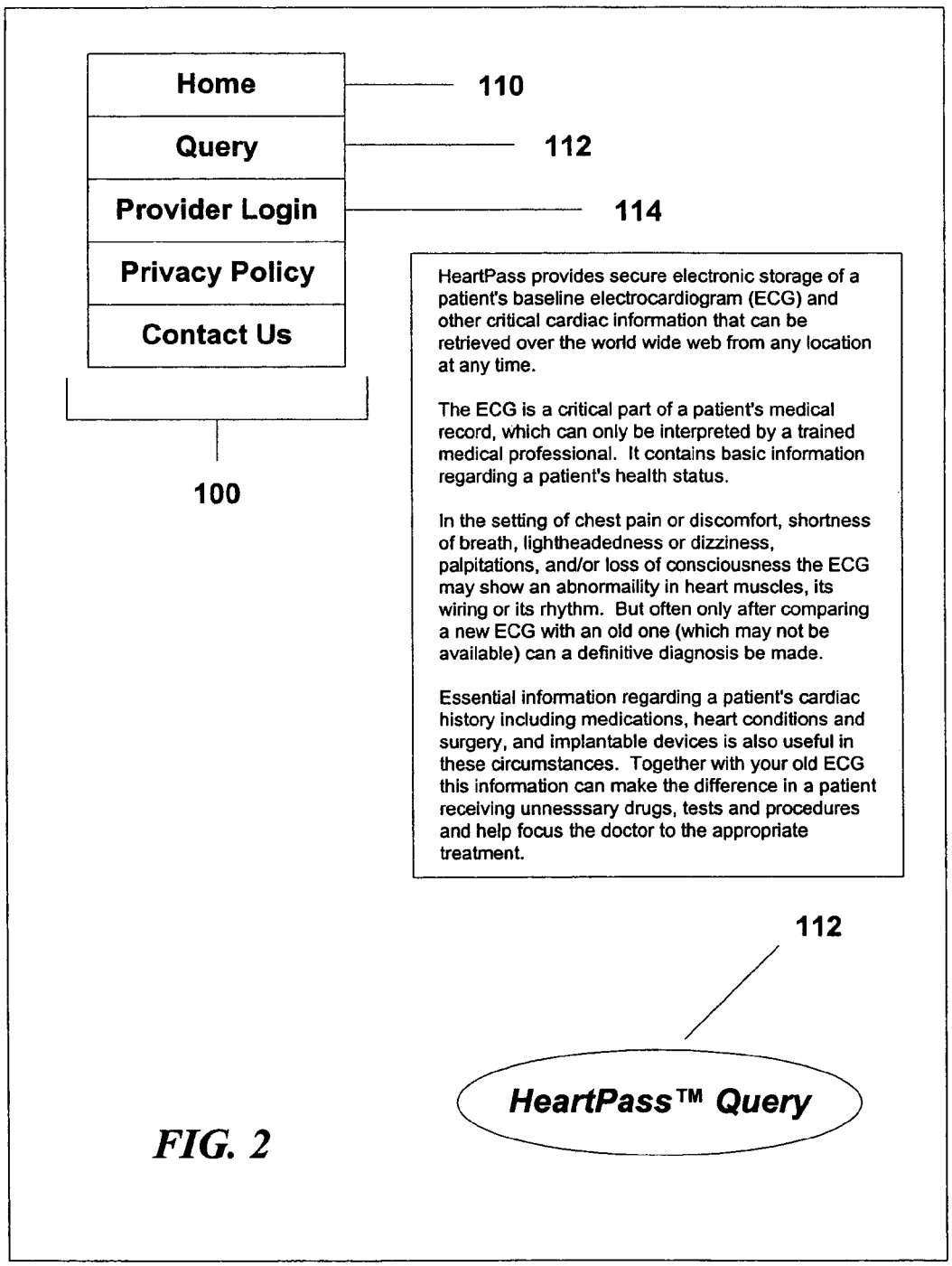
FIG. 2 shows a display of an introductory or home page that would be presented to a user.

FIG. 2 shows a display of an introductory or home page that would be presented to a user, as for example on the display unit of a computer. Computers are well known in the art and include a great variety of devices, including everything from Personal Digital Assistants to Desktop Computers. This embodiment of the present invention can include a server communicatively coupled to one or more client stations and communicatively coupled to the storage medium via one or more networks, such as the internet. The webpage shown is part of a Graphical User Interface, which allows a user to access a database through a menu 100 presenting a number of menu options. Information about the system and method can also be provided. A "Home" menu option 110 can include a link that brings the user to the home page. A "Query" menu option or link 112 may be provided to allow a user to request and access cardiological information on the database. As shown, option can be provided (e.g. linked) in any number of locations on the presented page. A "Provider Login" 114 can be configured to allow access to a user who is also a provider of the system and method.

At FIG. 3 is shown the display 200 when a user selects the "Provider Login" 114 option from FIG. 1. Access to the database could be prevented until the user provided a provider identifier 210 (e.g. a username or Provider ID 210 and password 220). Upon entering the correct input, the user could then login 221. The system would then recognize the user as a provider. If the provider identifier is not given, then access to the database is prevented. A provider is anyone who makes the system and method available to a user or patient; a provider may also be a user. For example, a health care professional such as a doctor may offer his or her patients the opportunity to use the system and store their medical records and other patient information on the database, making him or her a provider. That doctor may also make use of the invention to aid in treating the patient. In another example, the provider could be a heath care practice or office with many health care professionals. The health care professionals could each be given the practice's single provider identification information so as to allow shared coverage of patients (e.g.: to cross-cover patients on the weekend). Of course, a provider may not necessarily be a doctor, as for example where the provider is an insurance company. While the embodiment shown has one level of access for providers, providers could be classified and given differing degrees of access based on any number of factors. For example, an insurance company may be a provider insofar as they allow a patient or doctor to use the invention, but the insurance company may not be allowed access to certain medical records. In such a case, the provider's access could be limited to information that it is authorized to manage and see and otherwise restricted. Thus, there could be many different classifications and levels of access to the system and method based upon the type of user or any other factor (e.g., an administrator of the system could be granted or denied access based upon the provision of an administrator code). In any event, a heath care professional may control and confirm the input of specialized patient information to assure that the information enables a heath care professional to provide optimal care when it is accessed and displayed. This information can make the difference in a patient receiving unnecessary drugs, tests and procedures and help focus the doctor to the appropriate treatment.

Where the provider's login 221 is successful, the provider then is presented with a page 300 that gives a number of options, which are a function of the degree of provider's access, as shown at FIG. 4. Where the provider is a health care professional, the provider is given the option to enroll a new patient 310 into the database. The provider is also given the option to access the cardiological patient information of a patient associated with the health care professional. For instance, to obtain a patient's cardiological patient information the provider can choose to display all of the patients to which the provider has access 320, or search the patients 330 to which the provider has access by a useful index (e.g. last name in alphabetical order). Options such as termination 321 and renewal of a user's use of the system may also be provided as an option.

FIG. 5 shows the page displayed when the provider is given the option to enroll a new patient 310 into the database. The provider is presented with a screen where he or she may input information about the patient, including cardiological patient information. The provider can enter identification information about a patient 400 being enrolled, and the medical history 422 of the patient, the cardiac history of the patient 432, including any history of any implants 434 the patient may have. Non-limiting examples of the information that may be requested of an enrolling patient follow.

The identification information about a patient 400 may include patient information, including:
a user password (e.g. "HeartPass Password") 410
Last Name 412;
First Name 414;
Address 416;
Date of Birth (MM/DD/YY) 418; and
Email Address 420.
Any one or more of these identifiers may be included.

The cardiological patient information may comprise a medical history 422 of the user, which can include a cardiologically relevant medical factor. Examples include Hypertension, CNS Bleed; Diabetes, GI Bleed, Asthma, Anemia, Chronic Obstructive Pulmonary Disease, Deep Vein Thrombosis, Chronic Renal Insufficiency, Pulmonary Embolus, Hemodialysis, Inferior Vena Cava Filter, Cerebral Vascular Accident, Carotid Endarterectomy, or Transient Ischemia Attack. The medical history factors can also include a malignancy 424, an allergy 428, a medication 430, and any other factor that may impact cardiac health 426 (e.g., "Miscellaneous"). Any one or more of these factors, as well as any one or more other cardiologically relevant factors, may be selected and included as a cardiological relevant factor.

The cardiological patient information may also include a cardiac history of the patient comprising a cardiologically relevant cardiac. Exemplary factors include: Neurocardiogenic Syncope, Cardiomyopathy, Orthostatic Syncope, HOCM/IHSS, Syncope due to Autonomic Dysfunction, Cardiac Transplant, Coronary Artery Disease, Abdominal Aortic Aneurysm, Myocardial Infarction, AAA Repair, Coronary Artery Bypass Grafting, Congestive Heart Failure, Aortic Valve Replacement, a Ejection Fraction, Mitral Valve Replacement, and data regarding Percutaneous Coronary Intervention."). Any one or more of these factors, as well as any one or more other cardiologically relevant factors, may be selected and included as a cardiological relevant factor. Ample space may be provided to document factors such as a coronary artery bypass graft, type, location, and placement. In addition, the type and location of a coronary artery stent may also be recorded in a similar fashion.

The history of any implants 434 the user may have may include a Permanent Pacemaker (PPM) 436, an ICD 438, a BiVentricular Device 440 or an Implantable Loop Recorder 442, and a stent. Any one or more of these implants, as well as any one or more other implants, may be selected and included as a cardiological relevant factor. The implant history can include identifying information about the implant 442 (e.g.: the manufacturer). Identification information about implants a user may have received can be useful when treating a patient in an emergency situation. Many life-sustaining implanted devices are adapted to record and report on the problems or events that occur within a person. For example, a pacemaker treats bradycardia (slower heart rhythms). A pacemaker can sense, record and store information about the functioning of the device as well as any cardiac arrhythmia. A health care professional may access this information by using a device that interrogates the pacemaker and obtains information about its operating status as well as the stored information. As such, interrogating the implant can provide information that will clarify why a patient is symptomatic, be it due to device malfunction or physiological causes.

A common interrogation device is known as a programmer, which is a computerized device with a sensing wand that is waved over the pacemaker to obtain the information. However, several different manufacturers make different pacemakers, and commonly these different pacemakers will not respond an interrogation device adapted to retrieve information from another manufacturer's pacemaker. For example, a pacemaker made by Medtronic will only be responsive to a programmer that interrogates Medtronic pacemakers. If a treating health care professional does not know who the manufacturer is, he or she must have a number of different interrogating devices and must use each of them until discovering the right one. A treating health care professional, in the absence of information about the implant, is at a great disadvantage in providing optimal care since the information provided by the pacemaker can be vital to the course of treatment of the patient. The same is true of other implantable devices such as an implantable cardioverter-defibrillator, which can act as both a pacemaker and a defibrillator (which treats tachycardias or faster heart rhythms), or an implantable loop recorder. As such, when a patient is enrolled such that a user can have access to that information, a health care professional is positioned to provide optimal heath care when that information is transmitted and displayed to a user.

Once all the information about the enrolling patient has been gathered and inputted, the provider is given the option to move to the next step 444 after being cautioned to check the accuracy of the information. The provider is then taken to a page 500, shown at FIG. 6, where the provider can confirm the information entered about the enrolling patient that is displayed there. The patient is also given an identification number 510 that can be used to access the system. If the information presented is confirmed, the provider is given the option to continue to the next step 520; if not, the provider may activate a link, which presents them with the page shown at FIG. 5A, where the inputted information may be edited or inputted afresh. FIG. 5A may be substantially the same as FIG. 5, but may also have a number of differences, as for instance is shown by the link which now indicates that information about the user is being updated 446 (as opposed to being entered for the first time), or that an electrocardiogram may be edited 448 if entered into the database, as will be shown below. A user such as a health care professional can have access to the input update and editing functions of FIG. 5A at any time after enrolling a patient so as to keep current and accurate any information about the patient in the database. Again, upon inputting the information the provider will be given the option to confirm the information as shown in FIG. 6.

If the information presented is confirmed, and the provider chooses to continue 520, the provider is presented with a page 600 that allows him or her to upload an electrocardiogram (ECG) into the database, as shown in FIG. 7. The ECG may be uploaded from any number of sources, be it a digitized image such as one in the gif, jpeg, or pjpeg format that is scanned from a hard copy of an ECG, or be it directly from a electrocardiograph (or like recording device or method) which sends signals directly into a computer that translates the data into digital information which can be stored and presented in a graphic format that enables a health care professional to interpret the graphic. It will be understood that the precise format, system, or apparatus from which the ECG data is obtained and stored is not limited to the examples presented herein, as on skilled in the art will recognize that there are many ways in which to obtain and store data as well as present it in a graphic format- or any other format that can be readily interpreted by a health care professional. In the embodiment presented, the provider is given the option of accessing 610 his or her own files stored on a computer by "browsing", which is well known. The files to be uploaded stored in the database are shown as gif, jpeg, or pjpeg, but may be any format, as has been discussed. After finding the enrolling patient's ECG, the provider may then upload 612 the image file. The provider may then continue to the next page 614, or choose to upload a replacement or additional ECG. While the abovementioned image is that of an ECG, it will be understood that other images that are useful in enabling a heath care professional to provide optimal care may be uploaded. For example, the upload and storage of an image may include: chest X Rays, echocardiograms angiograms CAT scan/MRI and nuclear images. Provisions from member agreement document to manage and administer said program may also be uploaded.

At FIG. 8 is shown a page 700 for entering payment information in order to process a payment. Access to the database can be offered to the patient for a user fee. Where a provider is offering the access, the provider may be offered a part of the fee for enrolling a patient (e.g, as reimbursement for, inter alia, uploading the information and verifying its accuracy). For example, storage and access to the database can be offered to the enrolling patient, identified by a user or patient identifier 710 for a yearly charge 712, which may be paid via electronic payment (e.g., online payment using a credit card). A heath care professional such as a doctor may offer access to the database to his or her patients, including those who he or she deems would gain the most benefit from the invention. As such, the doctor acts as a provider of the system, and the doctor could be offered a percentage of the yearly fee for each patient he or she enrolls. This incentive not only benefits the provider and the host of the system, but it benefits the patients enrolled. This is because access to the information can result in more efficient and accurate health care delivered to the patient. The health care professional, in reviewing, confirming, and having editorial control over the specialized patient information stored in the system can help ensure that the information optimizes any treatment related to the specialty that is later provided. The can be accessed from anyplace having internet access capability, as nearly all medical facilities do. This in turn provides a greater benefit to society as more efficient health care is ultimately less burdensome to the economy, promotes better health, and, of course, saves lives.

A page (not shown) may be provided to upload and store documents such as agreements between user parties (e.g.: between providers and member or patient users) so as to archive the terms and conditions for use of the database.

As was shown at FIG. 4 a provider has also the option to access the cardiological patient information of a patient associated with the health care professional. To obtain a patient's cardiological patient information the provider may choose to display all of the patients to which the provider has access 320, or search the patients 330 to which the provider has access by a useful index (e.g. last name in alphabetical order). If a provider chooses to display all of the patients 320, then the provider will be taken to a page 800 shown at FIG. 9 where the patients associated with the provider may all be presented as indexed by any number of useful user identifiers that identify or classify the patient. The identifiers can include and be selected from: a user identification number 810, a user identification password 812, a user name 814, 816, a user date of birth 818, an enrollment date 824, and an account status 826. Any one or more of these identifiers, as well as any one or more other identifiers, may be selected and included as a user identifiers. Although these exemplary user identifiers are used to identify a patient, user identifiers can also include identifiers that identify a provider where such identifiers are useful.

The provider 804 and the provider's ID 802 can be provided at the top of the page.

If the provider chooses to search the patients FIG. 4, 330 by some index (e.g. last name in alphabetical order), they will be taken to a page such as shown at FIG. 11. There the patients are presented, for example, by last name in alphabetical order 52, with a linked alphabetized index 50. Thus if a provider user selects "A", he or she will be provided with all the patients that he or she may access with the last name A. If the provider chooses to terminate or renew a patient FIG. 4, 321, he or she will be taken to a page such as the one shown at FIG. 11A.

In either case, for each patient listed is an option to display that patient's cardiological patient information 820, and the option to edit that patient's cardiological patient information 822. Editing a patient's information is an option that may be restricted to health care professionals, as was discussed in relation to FIG. 5A. In any case, it is beneficial to allow a health care professional to alter the stored cardiological patient information if it needs changing or updating. As such, the health care professional may be given access to edit and upload information as necessary or desired, and may be given Read and Write access.

FIG. 10 shows a display of the cardiological patient information that is configured to enable to provide optimal care. Any information about a patient that was inputted and stored is presented such that it allows a treating physician to readily assess all the factors that impact a patient cardiac health. So too, by having this information readily available, if access is provided to an entity giving emergency treatment to the enrolled patient, the treating entity will be able to provide the most effective care. The medical history 910, including allergies 912 and medications 914 that the patient is on, is presented. Alongside, but separately presented is the patient's cardiac history 916, allowing for a more targeted assessment of the patients health. For example, the cardiac history will include information about any implant devices and the implant's manufacturer, the advantages of which have been described above in relation to FIG. 5.

Also shown is the uploaded ECG image 920. The ECG is a critical part of a patient's medical record, which can usually only be interpreted by a trained health care professional. It contains basic information regarding a patient's heart status. In the setting of chest pain or discomfort, shortness of breath, lightheadedness or dizziness, palpitations, and/or loss of consciousness the ECG may show an abnormality in heart muscles, its wiring or its rhythm. After comparing a new ECG with an old one, a definitive diagnosis be made. By virtue of having a patient's prior ECG, a treating professional can make a ready diagnosis. As discussed, targeted information regarding a patient's cardiac history including medications, heart conditions and surgery, and implantable devices is also useful in these circumstances. Together with a prior ECG this information can make the difference in a keeping patient from receiving unnecessary drugs, tests and procedures and helping focus the doctor to the appropriate treatment.

As shown at FIG. 12, an enrolled user, member, or entity granted access that is not a provider can access the stored information, via a login page 60 by entering a user identifier 62 such as a patient or member ID and a password 64. If the correct information is entered, the user is then taken to a display of the cardiological patient information that is configured to enable a heath care professional to provide optimal care, as shown at FIG. 10 A, which is substantially the same as FIG. 10. If, however, the user does not have the requisite degree of access, as might a provider that is health care professional, then they will not be given the option to update or otherwise alter the information in the database (e.g.: the non-provider user is granted Read Only access). The patient could be informed before the information is displayed that the uploading and verification of correct information is solely the responsibility of their health care professional (e.g., a provider who is a cardiologist), as shown at FIG. 12, 66. All the information related to a patient's ECG and medical history can be de-identified and Health Insurance Portability and Accountability Act (HIPAA) compliant. HIPAA regulates the protection and release of a patient's medical information. As such, the access may be provided to an entity giving emergency treatment to the enrolled patient (e.g. by inputting the patient's user's member identification and password to receive the HIPAA compliant cardiological information).

Another embodiment of the present invention is directed to a client-server system and/or method for providing a user with electronic access over a network to medical history information. As shown in FIGS. 1 and 13 this embodiment of the present invention can include a storage medium having electrocardiogram or other medical information stored thereon, such as a database or file. It should be understood that the storage medium can utilize any logical arrangement of medical or related data and such data may be arranged in fewer or more tables, databases, or files. Further, such data could be stored, as part of any one or more of the components of the present invention, and any of the one or more databases could be accessible, via a communicative coupling, to any of the aforementioned components of the present invention.

This embodiment of the present invention also can include a client station, including, but not limited to a computer, telephone, scanner, cell phone, facsimile machine, PDA or other internet equipped processing device, having a user interface configured to allow a user to request stored electrocardiogram information. This embodiment of the present invention can further include a server communicatively coupled to one or more client stations and communicatively coupled to the storage medium via one or more networks, such as the internet, the server configured to receive the request for electrocardiogram information from the user, retrieve the requested electrocardiogram information, and transmit the requested electrocardiogram information to the client station of the user. In another embodiment of the invention, the information is requested over the telephone, via touch-tone control, voice recognition systems or other system for transmitting information. The data can then be faxed to the requester.

The electrocardiogram, chest X Rays, echocardiograms angiograms CAT scan/MRI, nuclear image or other medical information transmitted or downloaded to the client station of the user can be displayed on a web page, or alternatively, can be transmitted to the user via a telephone, facsimile, email, or other method of electronic data transmission. The medical information can also be electronically provided or uploaded by a user to the storage medium on a web page or alternatively, can be provided via a scanner, facsimile, email, or other method of electronic data transmission.

In one embodiment of the invention, the users of the system, such as patients or doctors, can register through usernames and/or passwords, cookies, and the like, electronically via a web page or other manner. They can belong to a group in which they are charged a periodic (e.g., monthly or annual) fee to use the system. In certain embodiments, a user, who is a patient, may receive a discount or a credit to their account or bill where they choose to upload information on their own. In certain embodiments, a doctor can become a provider of the system to the user for free or a fee. For example, a patient may choose to have his or her medical information uploaded to the storage medium of the system by their doctor, doctor's staff, or personnel of the system provider (where the provider is different from their doctor). However, the patient may be provided an incentive where the patient chooses to upload his or her own medical information to the system, such as by receiving a credit or discount on his or her periodic fee for being a system group member. Where the doctor uploads a patient's information to the system, the doctor may be entitled to the fee or receive a discount or credit on the doctor's periodic fee for being a system group member, in return for the overhead costs associated with updating and maintaining the system as it relates to their patients.

Each user of the system may be provided with a secure password and/or a UserID, ID#, or UPIN# which allows the user to store and retrieve the medical information. The user may electronically communicate his or her password via a user interface on their client station, such as via a web page, to the server. The server can then determine whether the user is authorized to access the system or store or retrieve information on the system, by comparing the password and/or UserID (or cookie and the like) entered by the user, such as in the log in box (FIG. 14) with a data file or other storage medium containing a list of authorized users. A web page may provide for separate Login by registered members depending on whether they are doctors, practitioners, or patients, and may require the user to provide a username and password to determine whether to allow authorization. There can also be different levels of access for different types of users. However, the system can be set up such that patient consent is obtainable before any type of use is made of their data. After the server determines that the user is authorized to access the system, the user may then log in to the system and request electrocardiogram or other information for a patient, such as by the corresponding patient's name, such as in FIG. 15. The user may be provided with a list of information, which he or she may be authorized to access, such as shown in FIG. 16. Where the user is a doctor, the user may be provided with a list of his or her patients or those of his or her practice upon log in to the system and may select a patient to view their electrocardiogram information. Alternatively, the doctor or other non-patient user can be required to enter a specific patient identifier. Further, the doctors or other medical professional can be members who belong to a specific medical practice or group and each member may be authorized to retrieve the information for any shared patients or patients belonging to members of the group. The information relating to patients in such a group may be stored on a separate database or file, or may be allotted a certain portion or address within a database or file, which includes multiple groups of related patients.

Alternatively, the server may again determine whether the particular user is authorized to retrieve the particular information requested or store the information provided. For example, a user may be a doctor who is only authorized to retrieve information regarding their own patients (or that of their practice's patients, as is common in a medical practice) or provide information for storage regarding their own patients (or that of their practice's patients, as is common in a medical practice). On the other hand, a user may be a patient who is only authorized to retrieve his or her own information. In certain instances, the owner of the electrocardiogram information may choose to provide authorization to certain other users to allow full or limited access to their information. Also, the electrocardiogram itself may be encrypted or otherwise secured. Since to the untrained eye an electrocardiogram appears as lines and squiggles and can usually only be interpreted correctly by a trained health professional, the electrocardiogram can be provided to the user without a corresponding written interpretation of the electrocardiogram, assuring that the electrocardiogram is only useful to a healthcare professional. This also is a form of security for the electrocardiogram. Such written corresponding interpretation may be removed before or after storage of the information. The method of storing the medical information, the data backup and/or archival procedure, and the retrieval of the medical information can all be performed in accordance with HIPAA regulations in order to protect the privacy of the patient. One example of a display of a stored electrocardiogram is shown at FIG. 17.

In certain embodiments of the present invention, users of the system or method may use smartcard or implantable chip technology to retrieve or download specialized patent information to a disk, CD, flash memory stick, or other storage medium device, such as a smartcard or implantable chip, which contains a microchip that allows a user to store their information or their patients' information on their smartcard or implantable chip. Additionally, users of the system may provide or upload electrocardiogram information from their storage medium, such as a smartcard or implantable chip, to the storage medium of the system for later retrieval. Furthermore, certain medical profile information which may be contained in a medical data base or storage system such as a smartcard or implantable chip (such as age, gender, history of heart disease, heart disease risk factors such as smoking history, diabetes, family history of heart disease or arrhythmias or and abnormal ECG, hypertension, obesity, and high cholesterol) can help to select those who could benefit the most from a premium medical information or ECG storage and retrieval service. In certain embodiments, information relating to a patient stored on a storage medium, such as a medical database or smartcard or implantable chip, is processed to create a cardiac profile or other medical profile for a patient, wherein such profile may include risk factors in order to determine who should receive and benefit from the system or method described by the present invention. Further, each user or member of a group may be provided with a physical hard copy (e.g.: a laminated card) of their own or their specialized patient information, for example, a patient history and/or an image which is stored on the system, such as an image of a patient's electrocardiogram. Their implantable devices or materials and their ID# and password may also be provided.

Although the invention's specialized information about a patient has been described using the example of cardiological patient information, any other forms of specialized information are contemplated. Non-limiting examples of other sub-specialty-centric systems or organ-centric systems include neurological information such as that containing information regarding a patient with central nervous system disorders; the relevant medications and/or diseases, as well as CT/MRI image or images could be stored and displayed. Psychological, psychiatric, or other Psycho-centric information could also be used, including a patient's DSM IV diagnosis and psychotropic medications. Nephrological information may be used in the invention, including BUN/Cr, Dialysis information. Other subspecialties include oncology, endocrinology, gastroentology, musculo-skeletal (e.g.: Rheumatology and orthopedics), and internal medicine (not limited to age, race, or any other category of patient). So too, could radiological information with the relevant images be used. It will be understood that sub-specialties of specialized patient information may be targeted or categorized in any manner to optimize a patient's health. For example, the specialized patient information may comprise information related to diabetes or dialysis. Hence the specialized patient information may be disease entity-centric or treatment oriented.

The invention has been described in connection with certain drawings and exemplary, non-limiting embodiments. It should be understood that the above description is only representative of illustrative embodiments and examples. For the convenience of the reader, the above description has focused on a limited number of representative examples of all possible embodiments, examples that teach the principles of the invention. The description has not attempted to exhaustively enumerate all possible variations or even combinations of those variations described. That alternate embodiments may not have been presented for a specific portion of the invention, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the invention. It should be clear to those skilled in the art and from the teachings herein that various modifications, additions, and subtractions can be made without departing from the spirit or scope of the invention. Accordingly, the invention is not intended to be limited to less than the scope set forth in the following claims and equivalents.

The invention claimed is:

1. A method of providing specialized patient information, comprising:
   electronically acquiring specialized patient information, via a specially programmed computer server, from at least one of a plurality of patients, wherein each patient personally enters a part of the specialized patient information utilizing at least one of:
      (a) a specifically programmed on-line user interface of a first internet equipped electronic device and
      (b) a specifically programmed user interface of a first portable electronic device;
   wherein the specialized patient information of said patient comprise at least all of the following:
   i) past medical history of such patient, at least identifying whether such patient is taking at least one medication and has at least one allergy;
   ii) cardiac history of such patient, at least identifying that such patient has or has not had at least one of the following:
      1) coronary artery disease,
      2) heart surgery,
      3) percutaneous intervention,
      4) congestive heart failure, and
      5) at least one implantable device;
   iii) an electrocardiogram of such patient;
   storing, via the specifically programmed computer server, the acquired specialized patient information in a computer database;
   responsive to the successful storage of the specialized patient information in said database, electronically requiring said patient to enter patient identification information to access the specialized patient information, wherein the patient identification information is selected from the group consisting of: a user identification number, a user identification password, a user name, a user address, a user data of birth, a user email address, an enrollment date; and an account status, or any combination thereof; wherein each patient personally enters the patient identification information utilizing at least one of:
      (a) a specifically programmed on-line user interface of a second internet equipped electronic device and
      (b) a specifically programmed user interface of a second portable electronic device;
   electronically transmitting, via the specially programmed computer server, the specialized patient information to a specifically programmed electronic portable device of the provider or a specifically programmed internet equipped electronic device of the provider; wherein the provider is the patient's doctor;
   electronically requiring said provider pay a provider fee for access to the acquired specialized patient information; wherein upon receipt of the provider fee, the provider may review, confirm, and have editorial control over the specialized patient information, to help ensure that the specialized patient information optimizes any treatment related to the patient.

2. The method of claim 1, wherein the cardiac history comprising a cardiologically relevant factor.

3. The method of claim 2, wherein the cardiologically relevant factor is selected from: Hypertension; CNS Bleed; Diabetes; GI Bleed; Asthma; Anemia; Chronic Obstructive Pulmonary Disease; Deep Vein Thrombosis; Chronic Renal Insufficiency; Pulmonary Embolus; Hemodialysis; Inferior Vena Cava Filter; Cerebral Vascular Accident; Carotid Endarterectomy; Transient Ischemia Attack; a malignancy; an allergy; and a medication.

4. The method of claim 2, wherein the cardiologically relevant factor is selected from: Neurocardiogenic Syncope; Cardiomyopathy; Orthostatic Syncope; HOCM/IHSS; Syncope due to Autonomic Dysfunction; Cardiac Transplant; Coronary Artery Disease; Abdominal Aortic Aneurysm;

Myocardial Infarction; AAA Repair; Coronary Artery Bypass Grafting; Congestive Heart Failure; Aortic Valve Replacement; Ejection Fraction; Mitral Valve Replacement; and data regarding Percutaneous Coronary Intervention.

5. The method of claim 2, wherein the cardiologically relevant factor further comprises the history of the at least one implantable device.

6. The method of claim 1, wherein the provider fee is a periodic fee.

7. The method of claim 6, wherein the periodic fee is selected from the group consisting of: monthly and annually.

8. The method of claim 1, wherein the specialized patient information includes an image.

9. The method of claim 1, wherein the implant is selected from:
   a Permanent Pacemaker;
   an ICD;
   a stent;
   a BiVentricular Device; and
   an Implantable Loop Recorder.

10. The method of claim 1, wherein the provider is an entity giving emergency treatment to the patient.

11. The method of claim 1, wherein the specialized patient information comprises at least one of the following types of information: neurological patient information; psycho-centric patient information; nephrological patient information; radiological patient information; musculo-skeletal patient information; oncological patient information; patient information related to internal medicine; endocrinological patient information; or gastroenterological patient information.

12. The method of claim 1, wherein the first internet equipped electronic device and the second internet equipped electronic device are the same device.

13. The method of claim 1, wherein the first portable electronic device and the second portable electronic device are the same device.

* * * * *